United States Patent
Ferruti et al.

(10) Patent No.: US 8,840,875 B2
(45) Date of Patent: Sep. 23, 2014

(54) ANTI-VIRAL AGENTS AND COMPOSITIONS THEREOF

(71) Applicants: Paolo Ferruti, Milan (IT); Elisabetta Ranucci, Opera (IT)

(72) Inventors: Paolo Ferruti, Milan (IT); Roberta Cavalli, Alessandria (IT); Elisabetta Ranucci, Opera (IT); David Lembo, Turin (IT)

( * ) Notice: Subject to any disclaimer, the term of this patent is extended or adjusted under 35 U.S.C. 154(b) by 0 days.

(21) Appl. No.: 13/886,364

(22) Filed: May 3, 2013

(65) Prior Publication Data
US 2013/0243721 A1    Sep. 19, 2013

Related U.S. Application Data

(63) Continuation of application No. 13/698,469, filed as application No. PCT/IB2011/052163 on May 17, 2011, now abandoned.

(30) Foreign Application Priority Data

May 19, 2010   (IT) .............................. TO2010A0415

(51) Int. Cl.
*A61K 31/785*   (2006.01)
*C08G 69/02*   (2006.01)
*C08G 73/02*   (2006.01)

(52) U.S. Cl.
CPC .............. *C08G 69/02* (2013.01); *A61K 31/785* (2013.01); *C08G 73/028* (2013.01)
USPC ....................................... 424/78.35; 528/310

(58) Field of Classification Search
None
See application file for complete search history.

(56) References Cited

FOREIGN PATENT DOCUMENTS

EP    1 881 020 A1    1/2008

OTHER PUBLICATIONS

Vippagunta et al. "Crystalline Solids," Advanced Drug Delivery Reviews, 2001, 48, pp. 18.*
Müller, Inorganic Chemistry, p. 14-15, 1993.*
HIV Infections, MedlinePlus Medical Encyclopedia, retrieved from http://www.nlm.nih.gov/medlineplus/ency/article/000602.htm, Jan. 17, 2014.*
Franchini et al., "Synthesis, Physicochemical Properties, and Preliminary Biological Characterizations of a Novel Amphoteric Agmatine-Based Poly(amidoamine) with RGD-Like Repeating Units", Biomacromolecules 2006, 7, 1215-1222.*
Jacchetti, et al., "Biomimetic poly(amidoamine) hydrogels as synthetic materials for cell culture." Journal of Nanobiotechnology, vol. 6, No. 14, pp. 1-15, Nov. 17, 2008.

* cited by examiner

*Primary Examiner* — Ernst V Arnold
*Assistant Examiner* — Jianfeng Song
(74) *Attorney, Agent, or Firm* — Silvia Salvadori, P.C.

(57) ABSTRACT

Guanidine-based poly (amidoamine) polymers of formula (I): wherein n is an integer between 3 and 400; $R_1$ is H, $C_{1-6}$ alkyl; or taken together with the N atoms to which is bound and $R_2$ is a piperazinic ring; $R_2$ is $C_{2-6}$ alkylen; $C_{5-6}$ cycloalkylen; CH—COOH, CH—COOR, wherein R is $C_{1-4}$ alkyl, phenyl or benzyl; $R_3$ is —$(CH_2)$p-HN—C($NH_2$)=NH, wherein p is an integer 1 to 6; for use as antiviral agents in the prevention and/or treatment of viral infections in a mammal, preferably a human subject.

19 Claims, 3 Drawing Sheets

A)

B)

ANTI-VIRAL AGENTS AND COMPOSITIONS THEREOF

This application is a continuation of U.S. application Ser. No. 13/698,469 filed on Nov. 16, 2013, which is a 371 U.S. national phase of International Application PCT/IB2011/052163 filed on May 17, 2011, which claims priority to and the benefit of Italian Application No. TO2010A000415 filed on May 19, 2010, all of which are incorporated by reference herein in their entirety.

FIELD OF THE INVENTION

This disclosure concerns anti-viral agents and pharmaceutical compositions containing such anti-viral agents.

BACKGROUND

Human papillomaviruses (HPV) are members of the Papillomaviridae family of DNA viruses. More than 100 HPV types have been identified so far, over 30 of which infect the genital area. Genital HPV infections are estimated to be the most common sexually transmitted infections (STI). Although the majority of infections cause no symptoms and are self-limiting, genital HPV have become a major public health concern because persistent infection with certain types can cause cervical cancer which kills about 250,000 women worldwide each year. Genital HPVs are classified by their association with cervical cancer. Infection with low-risk types (primarily types 6 and 11) can cause benign or low-grade cervical cell changes and genital warts and are not associated with cervical cancer. Infection with high-risk types (primarily types 16, 18, 31, and 45) can cause low-grade and high-grade cervical cell abnormalities that are precursors to cancer and cervical cancer.

Cervical cancer is relatively uncommon in countries where widespread cervical Pap testing detects precancerous lesions before they can develop into cancer. In many developing countries where screening activities are limited, cervical cancer is the most common cancer in women. HPVs have also been implicated in a substantial fraction of other anogenital cancers at other anatomic sites, including the vulva, vagina, penis and anus.

No direct antiviral cure or treatment is currently available. Regular Papanicolau screening (Pap test), followed by ablative treatment of any abnormalities when detected, prevents HPV progression to cervical cancer.

Recently, highly effective vaccines were approved for interventions to prevent infection by four HPV types which together cause about 70% of cervical cancers (HPV-16 and HPV-18) and 90% of genital warts (HPV-6 and HPV-11) worldwide. The vaccine protects women only from contracting HPV infections of the types they have not yet encountered, and it should be administered to young women before they become sexually active in order to ensure maximum benefit. However, vaccinated women may remain exposed to the risk of becoming infected with some types of high-risk HPV that can cause cervical cancer but are not targeted by the current vaccine. Moreover, the vaccine is expensive and its cost could be prohibitive, especially for women in underdeveloped countries.

Within this scenario, a topical microbicide that could block the full spectrum of genital HPV infections at the portal of entry would provide a useful complement to vaccination programs.

Herpes simplex viruses (HSV) type 1 and 2 (HSV-1 and HSV-2) are closely related pathogens of the Herpesviridae family of DNA viruses. Both cause a lifelong, latent infection for which there is no cure or available effective vaccine. HSV-1 is usually transmitted via non-sexual contact and is generally clinically associated with oro-labial infection, whereas HSV-2 is typically transmitted sexually and infects anogenital sites. However, HSV-1 and HSV-2 are both capable of infecting mucosal sites, irrespective of their anatomic localization, and can produce clinically indistinguishable lesions. RSV infection causes various forms of disease, from lesions on the lips, eyes or genitalia to encephalitis or disseminated disease. The seroprevalence of HSV-1 spreads gradually from childhood, reaching up to 70-80% of the adult population worldwide, whereas HSV-2 seroprevalence rises after initiation of sexual activity and increases through adulthood (range, 5-25%). Women are more susceptible to HSV-2 infection than men. HSV-2 infection is a major public health problem and the most frequent cause of recurrent genital ulcer disease, with a high seroprevalence among young adults. Many infected individuals, often unaware of their serostatus, shed HSV asymptomatically and so may sexually transmit the infection.

HSV infection can result in a number of severe complications particularly in neonates, often resulting in disseminated disease with high morbidity and mortality, as well as stromal keratitis, a corneal infection that can lead to blindness. HSV infection also produces serious complications in the immunocompromised in whom severe recurrence and occasionally disseminated infection more readily occurs.

A notoriously close relationship exists between HSV and HIV infection: HIV infection increases both the risk and the morbidity of HSV infection, while genital ulcer disease, primarily associated with HSV-2, clearly enhances transmission of HIV-1 infection.

Strategies that can prevent HSV infection are expected to reduce rates of sexual HIV transmission and vice versa.

Acyclovir, a nucleoside analogue, is the antiviral drug of choice for treating HSV infection in the immunocompetent and the immunosuppressed because of its efficacy and lack of toxicity. But like other anti-herpetic agents for treating HSV infection, acyclovir fails to eradicate the virus from infected cells and to prevent reinfection/reactivation of HSV because, although it reduces the production of new viral particles, it cannot counteract early HSV infection.

Inhibitors of the early phase of HSV infection, including viral attachment and entry, are still lacking.

New therapeutic approaches are therefore highly desirable.

SUMMARY OF THE INVENTION

Taking into account these premises, the need is therefore felt for antiviral agents able to prevent and/or treat viral infections in mammals.

The object of this disclosure is providing such improved solutions.

According to the invention, the above object is achieved thanks to the subject matter recalled specifically in the ensuing claims, which are understood as forming an integral part of this disclosure.

An embodiment of the present disclosure provides the use of guanidine-based poly(amido-amine) polymers of formula (I):

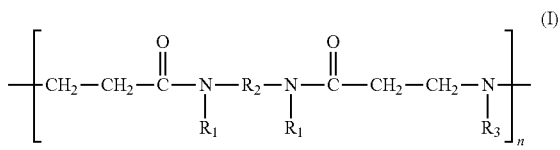

(I)

wherein n is an integer between 3 and 400;
$R_1$ is H, $C_{1-6}$ alkyl; or taken together with the N atoms to which is bound and $R_2$ is a piperazinic ring;
$R_2$ is $C_{2-6}$ alkylen; $C_{5-6}$ cycloalkylen; CH—COOH, CH—COOR, wherein R is $C_{1-4}$ alkyl, phenyl or benzyl;
$R_3$ is —$(CH_2)$p-HN—$C(NH_2)$=NH, wherein p is an integer 1 to 6,
as anti-viral agents for the prevention and/or treatment of viral infections in mammals, preferably human beings.

A further embodiment, of the present disclosure concerns pharmaceutical compositions comprising guanidine-based poly(amido-amine) polymers of formula (I) for the prevention and/or treatment of viral infections in mammals, preferably in human beings. Such compositions may be administered via oral, parenteral, topical, rectal, ophthalmic, nasal, or vaginal route.

BRIEF DESCRIPTION OF THE DRAWINGS

The invention will now be described, by way of example only, with reference to the enclosed figures of drawing, wherein.

DETAILED DESCRIPTION OF THE INVENTION

Figure 1:
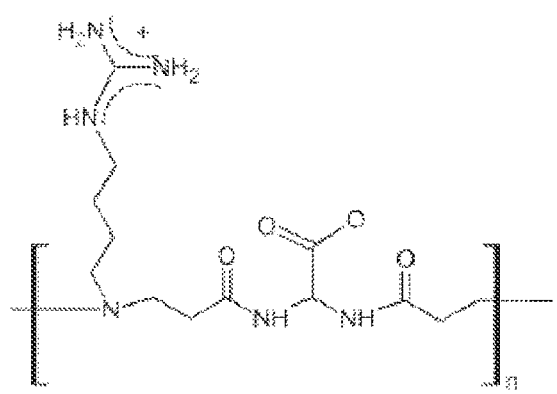
FIG. 1. Chemical structure of AGMA-1 polymer.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

4-Aminobutyl guanidine, or agmatine, belongs to the family of biogenic amines involved in many physiological functions. These biomolecules play an important role in cell growth and proliferation, as well as in the synthesis of proteins and nucleic acids. Moreover, agmatine is endowed with a large number of properties, e.g., in the neuronal, vascular, and metabolic fields. Agmatine derives from the arginine decarboxylase (ADC)-mediated decarboxylation of L-arginine, a semi-essential amino acid with interesting properties mostly attributed to its guanidine group. The tripeptide arginylglycylaspartic acid (RGD) is an oligopeptide capable of reproducing the receptorial sites of proteins, such as fibronectin, vitronectin, and others playing a fundamental role in cell adhesion. Grafted on a material's surface, RGD is capable of promoting a strong cell adhesion even at very low surface densities. The RGD sequence gained much interest in the past decade for its astounding properties. Based on this premise, the present inventors introduced agmatine-deriving units in poly(amido-amine)s (PAAs) as disclosed i.a. in the Italian patent IT1355868.

Poly(amidoamine)s (PAAs) are synthetic biodegradable polymers that can be designed to be highly biocompatible. They were first, described in 1970 [Danusso and Ferruti P. (1970)] and, subsequently, their physico-chemical and biological properties were reviewed in several instances [Ferruti, Marchisio and Barbucci (1985); Ferruti, (1996); Ferruti, Marchisio and Duncan (2002)]. PAAs are obtained by stepwise Michael-type polyaddition of primary or secondary amines to bis-acrylamides, and carry amide (a) and teramine (b) groups regularly arranged, along the polymer chain in sequence either a..a..b..b or a..a..b, according to the type of amine monomer employed. PAAs should not be confused with the dendrimer-like polymers called PAMAM, which have different general formula and molecular architecture, are prepared by self-polyaddition of amino-substituted acrylamides and were described considerably later.

Many PAAs exhibit a combination of properties imparting them a considerable potential in the biomedical field. They are usually degradable in water at a rate depending on their structure. Therefore, if injected, they are bioeliminable. Most PAAs are only moderately toxic despite their polycationic nature. According to a number of tests, the toxicity of most PAAs is significantly lower than that of poly-L-lysine (PLL) or polyethyleneimine (PEI) or PAMAM.

The present inventors designed the synthesis of linear amphoteric PAA polymers containing agmatine-derived groups by means of the Michael-type polyaddition of guadine-derived units with BAG [Franchini, Ranucci, Ferruti, Rossi and Cavalli, (2006)] and IT1365868).

The repeating units of such guanidine-based poly(amido-amine) polymers of formula (I) carry guanidine- and carboxyl groups and show a strong structural resemblance to the RGD sequence. These polymers were studied for some relevant physicochemical properties, such as solubility, hydrolytic stability at physiological pH, and acid-base behavior. Preliminary biological characterizations, namely cell toxicity and hemolytic activity, were also performed [Franchini, Ranucci, Ferruti, Rossi, and Cavalli, (2006); Ferruti, Franchini, Bencini, Ranucci, Zara, Serpe, Primo and Cavalli (2007)].

The present inventors identified—in an unexpected and surprising manner—that such guanidine-based poly(amido-amine) polymers of formula (I) present a potent antiviral activity, which can be exploited in pharmaceutical compositions for the treatment and/or prevention of viral infections in mammals, particularly in humans.

The present inventors investigated the antiviral activity of one of these guanidine-based poly (amido-amine) polymers, namely AGMA-1 the chemical structure of which is represented in FIG. 1, versus HVP and HSV infections. More specifically, it emerged that AGMA-1 exhibited an inhibition of HPV-16 infection about 87% and 85% percentage, with a concentration of AGMA-1 at 33 μg/ml and 3.6 μg/ml, respectively. AGMA-1 presented an IC50 value of 0.74 μg/ml and 1.14 μg/ml against HSV-1 and HSV-2 infections, respectively. Furthermore AGMA1 inhibits HSV-2 infection in the model systems of Human 3-D Vaginal-Ectocervical Tissues.

In view of the foregoing, it can be stated that the guanidine-based poly(amido-amine) polymers of formula (I) can be used as active ingredients of pharmaceutical compositions for the treatment and/or prevention of viral infections.

The guanidine-based poly(amido-amine) polymers of formula (I) may be formulated with conventional carriers and excipients, which will be selected in accord with ordinary practice.

Excipients may include i.a. surfactants, preservatives, anti-oxidants, chelating agents, carbohydrates, hydroxyalkylcellulose, hydroxyalkylmethyl-cellulose, poloxamer, polymeric stabilizing agents and the like.

While it is possible for the guanidine-based poly(amido-amine) polymer(s) of formula (I) to be administered alone it may be preferable to present them as pharmaceutical compositions. The compositions of the invention comprise at least one guanidine-based poly(amido-amine) polymer, as above defined, together with one or more acceptable carrier and/or vehicle therefor and optionally one or more other therapeutic ingredients.

The carrier(s) and/or vehicle(s) must be 'acceptable' in the sense of being compatible with the other ingredients of the formulation and physiologically innocuous to the recipient thereof.

The pharmaceutical compositions include those suitable for different administration routes, like for example oral, rectal, ophthalmic (including intravitreal or intracameral), nasal, topical (including buccal and sublingual), vaginal or parenteral (including subcutaneous, intramuscular, intravenous, intradermal, intratracheal, and epidural) administration.

The pharmaceutical compositions may conveniently be presented in unit dosage form and may be prepared by any of the methods well known in the art of pharmacy. Such methods include the step of bringing into association the active ingredient with the carrier(s) which constitutes one or more accessory ingredients. In general the pharmaceutical compositions are prepared by uniformly and intimately bringing into association the active ingredient with liquid carriers or finely divided solid carriers or both, and then, if necessary, shaping the product.

When used for oral use for example, tablets, troches, lozenges, aqueous or oil suspensions, dispersible powders or granules, emulsions, hard or soft capsules, syrups or elixirs may be prepared.

Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. The oral formulations may contain the active ingredient (s) in an amount of, for example, 50 mg to 500 mg, preferably 100 mg to 400 mg, more preferably 150 mg to 300 mg.

For topical administration, e.g. mucous membrane and skin, the pharmaceutical compositions are preferably applied as topical ointments, gels, creams and pastes containing the active ingredient(s) in an amount of, for example, 2% to 90% w/w, preferably 5% to 60% w/w, more preferably 15% to 40% w/w. Formulations suitable for vaginal administration may be presented as pessaries, tamports, creams, gels, pastes, foams or spray formulations containing in addition to the active ingredient such carriers as are known in the art to be appropriate.

The topical formulations may desirably include a compound which enhances absorption or penetration of the active ingredient through the skin or other affected areas or other known antiviral agent(s).

Compositions suitable for parenteral administration include aqueous and non-aqueous sterile injection solutions or suspensions containing the active ingredient (s) in an amount of, for example, 2% to 50% w/w, preferably 5% to 30% w/w, more preferably 10% to 20% w/w.

The parenteral formulation may contain anti-oxidants, buffers, bacteriostats, suspending and/or thickening agents and solutes which render the formulation isotonic with the blood of the intended recipient. The compositions may be presented, for example, as sealed ampules and vials, and may be stored in lyophilized conditions.

Pharmaceutical compositions according to the present invention comprise one or more guanidine-based poly(amido-amine) polymer of formula (I) together with one or more pharmaceutically acceptable carriers or excipients and optionally other therapeutic agents.

The amount of guanidine-based poly(amido-amine) polymer(s) of formula (I) that may be combined with the carrier material to produce a single dosage form will vary depending upon the host treated, and the particular mode of administration.

Pharmaceutical compositions suitable for topical administration may comprise guanidine-based poly(amido-amine) polymer(s) of formula (I) in a concentration in the range of 0.1 mg/mL to 600 mg/mL.

Guanidine-based poly(amido-amine) polymer(s) of formula (I) can also be formulated to provide controlled release of the active ingredient to allow less frequent dosing or to improve the pharmacokinetic or toxicity profile of the active ingredient.

Accordingly, the invention also provided pharmaceutical compositions comprising one or more guanidine-based poly(amido-amine) polymer(s) of formula (I) formulated for sustained controlled release.

Example I

Synthesis and Characterization of AGMA-1 Polymer

Synthesis of AGMA-1.

Agmatine sulfate (2.000 g, 8.5 mmol) and lithium hydroxide monohydrate (0.360, 8.5 mmol) were added to a solution of 2,2-Bis-(acrylamido)acetic acid. (BAC) [synthesized according to Ferruti, Ranucci, Trotta, Gianasi, Evagorou, Wasil, Wilson and Duncan (1999)] (1.689 g, 8.5 mmol) and lithium hydroxide monohydrate (0.360 g, 8.5 mmol) in distilled water (2.8 mL). This mixture was maintained under nitrogen atmosphere and occasionally stirred for 72 h. After this time, it was diluted with water (2.8 mL), acidified with hydrochloric acid to pH 4-4.5, and then ultrafiltered through a membrane with nominal cutoff 3000. The fraction retained was freeze-dried and the product obtained as a white powder. Yield: 2.1 g. Its Molecular Weight values, as determined by SEC chromatography with Light Scattering on line, were $M_n$ 4800, $M_w$ 7200. The chemical structure of AGMA-1 is shown in FIG. 1.

Higher molecular weight samples with narrower distribution were obtained by adopting longer reaction times and ultrafiltering trough membranes with higher cut-off. For instance, the product obtained adopting a reaction time of 144 h and ultrafiltered through a membrane of cut-off 5000 gave 1.98 g of a sample with $M_n$ 12300 and $M_w$ 15600, while the product obtained adopting a reaction time of 216 hrs and ultrafiltered through a membrane of cut-off 10000 gave 1.75 g of sample with $M_n$ 38200 and $M_w$ 44500.

Example II

AGMA-1 Activity Against Human Papilloma Virus

Cell Culture.

The 293TT cell line derived from human embryonal kidney cells transformed with the SV40 large T antigen was cultured in Dulbecco's modified Eagle's medium (DMEM) (Gibco/BRL, Gaithersburg, Md., USA) supplemented with heat-inactivated 10% bovine serum (Gibco/BRL), Glutamax-I (Invitrogen, Carlsbad, Calif., USA) and nonessential aminoacids. This cell line allows high levels of protein to be expressed from vectors containing the SV40 origin due to overreplication of the expression plasmid (Buck et al., 2004).

Pseudovirion Production.

HPV-16 PsV were produced according to previously described methods (Buck et al., 2005a; Buck et. al., 2005b). Briefly, 293TT cells were transfected with the plasmid p16sheLL (Buck et al., 2006; Leder et al., 2001) expressing the papillomavirus major and minor capsid proteins (L1 and L2) together with a reporter plasmid expressing the secreted alkaline phosphatase (SEAP) or the green fluorescence protein (GFP) named pYSEAP or pfwB, respectively (Pastrana et al., 2004; Buck et al., 2005a; Buck et al., 2005b). Capsids were allowed to mature overnight in cell lysate; the clarified supernatant was then loaded on top of a 27-33-39% Optiprep (Sigma-Aldrich, St. Louis, Mo., USA) density gradient at room temperature for 4 h. The material was centrifuged at 234000×g for 3.30 h at 16° C. in an SW50.1 rotor (Beckman Coulter, Inc. Fullerton, Calif., USA) and collected by bottom puncture of the tubes. Fractions were inspected for purity on 10% SDS-Tris-glycine gels, titrated on 293TT cells to test for infectivity by SEAP or GFP detection, then pooled and frozen at −80° C. until needed. The L1 protein, content of PsV stocks was determined by comparison with bovine serum albumin standards in Coomassie-stained SDS-PAGE gels.

Inhibition Assays.

For the SEAP-based assays 293TT cells were preplated 3-4 h in advance in 96-well tissue culture-treated flat bottom plates at a density of 30,000 cells/well in 100 μl neutralization buffer (DMEM without phenol red, 10% heat-inactivated FBS, 1% glutamate, 1% nonessential amino acids, 1% penicillin-streptomycin-fungizone, and 10 mM HEPES). Diluted PsV stocks (80 μl/well) were placed on 96-well nontreated sterile, polystyrene plates (Nalge-Nunc, Roskilde, Denmark), combined with 20 ml of diluted AGMA-1 (33 μg/ml and 3.6 μg/ml), and placed on ice for 1 h. The 100-μl PsV-compounds mixture was transferred onto the preplated cells and incubated for 68-72 h. The final concentration of PsV was approximately 1 ng/ml L1. After incubation, 50 μl of supernatant were harvested and clarified at 1500×g for 5 min. The SEAP content in the clarified supernatant was determined using a Great ESCAPE SEAP Chemiluminescence Kit (BD Clontech, Mountain View, Calif., USA) as directed by the manufacturer. Ten minutes after the substrate was added, samples were read using a Lumino luminometer (Stratec Biomedical System, Birkenfeld, Germany).

Electron Microscopy.

An aliquot of diluted HPV-PsV preparations was placed on a grid and air dried prior to examination. Microscopy was performed using a Philips CM10 transmission electron microscope; micrographs were taken of random sections at different powers of magnifications.

Characterization of Purified HPV-16 PsV.

Figure 2:
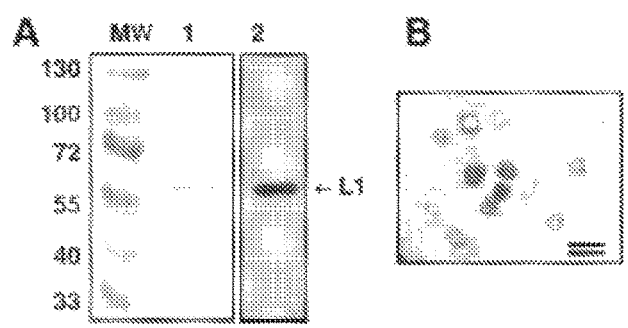
FIG. 2. Characterization of purified HPV-16-SEAP PsV.

HPV-16 was chosen as a model since it is the most oncogenic genital HPV type. To check the quality of the HPV-16-SEAP PsV preparation used in the subsequent assays, an aliquot was subjected to SDS-PAGE. As shown in FIG. 2A, a major band migrating at 55 kD was detected by Coomassie Brilliant Blue staining (lane 1) and was confirmed to be the L1 major capsid protein by Western blotting (lane 2). No L1-reactive proteolytic degradation products were observed at molecular weights below 55 kD, indicating the good quality of the preparation. FIG. 2B shows an electron micrograph of the same PsV stock. PsV routinely exhibited an average diameter of 50-60 nm, which is similar to that of an authentic HPV capsid, and appeared as individual, well-defined particles with minimal aggregation.

Inhibitory Effect of AGMA-1 Against HPV-PsV Infection.

Figure 3:
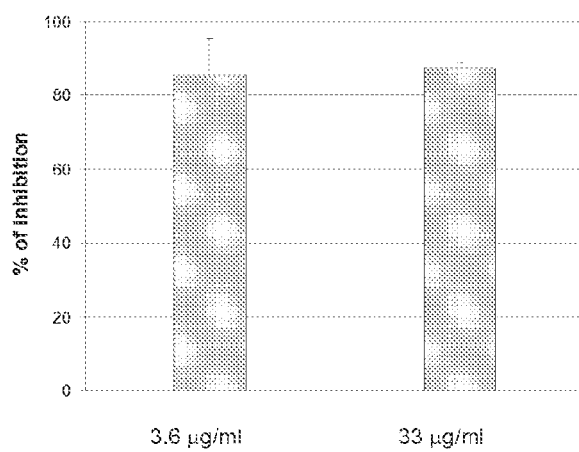
FIG. 3. Antiviral activity of AGMA-1 against HPV-16 PsV.

The early events of a PsV infection resemble those of a natural HPV infection since the PsV consists of a reporter plasmid encapsidated by a capsid composed of the two viral capsid proteins (L1 and L2) like an authentic HPV capsid. After PsV binding to and entry into the cell, the reporter plasmid is transported to the nucleus for expression of the reporter gene (Buck et al., 2004). The present inventors exploited a PsV-based assay to screen AGMA-1 compound as antagonist of HPV-16 infection. Two concentrations (3.6 μg/ml and 33 μg/ml) of AGMA-1 were preincubated with aliquots of HPV-16-SEAP PsV and then added to 293TT cell cultures. Inhibition of PsV-mediated delivery of the SEAP reporter plasmid 72 h post-infection was measured by chemioluminescence analysis of the cell supernatants. As shown in FIG. 3, AGMA-1 exhibited a strong inhibition of HPV-16-SEAP PsV infection of 87% and 85% percentage, respectively at 33 μg/ml and 3.6 μg/ml.

Example III

Antiviral Activity of AGMA-1 Against HSV-1 and HSV-2

Cells and Virus

African green, monkey fibroblastoid kidney cells (Vero) were grown as monolayers in DMEM supplemented with 10% of heat-inactivated fetal calf serum and antibiotics. HSV-1 and HSV-2 were used.

Virus Yield Reduction Assay

The effect of AGMA-1 on the production of infectious virus was assessed through a yield reduction assay in which cells were infected with the virus at a multiplicity of infection (MOI) of 0.01 pfu/cell in presence of serial dilutions of the compound. After 1 h adsorption, the virus inoculum was removed and cultures were again exposed to the compound. Surnatants from duplicate test condition were pooled as appropriate 72 h after infection and cell-free virus infectivity titers were determined in duplicate by the plaque assay in Vero cell monolayers. The end-points of the assay were the inhibitory concentrations of drug which reduced virus yield by 50% (IC50) versus the untreated virus control. The IC50 value for inhibition curves was calculated by using the program PRISM 4 (GraphPad Software, San Diego, Calif., U.S.A.) to fit a variable slope-sigmoidal dose-response curve.

Inhibitory Effect of AGMA-1 Against HSV-1 and HSV-2 Infections

To investigate whether the compound could inhibit the HSV-1 and HSV-2 infections, a virus yield reduction assay in monolayers of Vero cells infected with a clinical isolate of HSV-1 or HSV-2 was performed. The assay provides a stringent test, which allows multiple cycles of viral replication to occur before measuring the production of infectious viruses.

Figure 4:
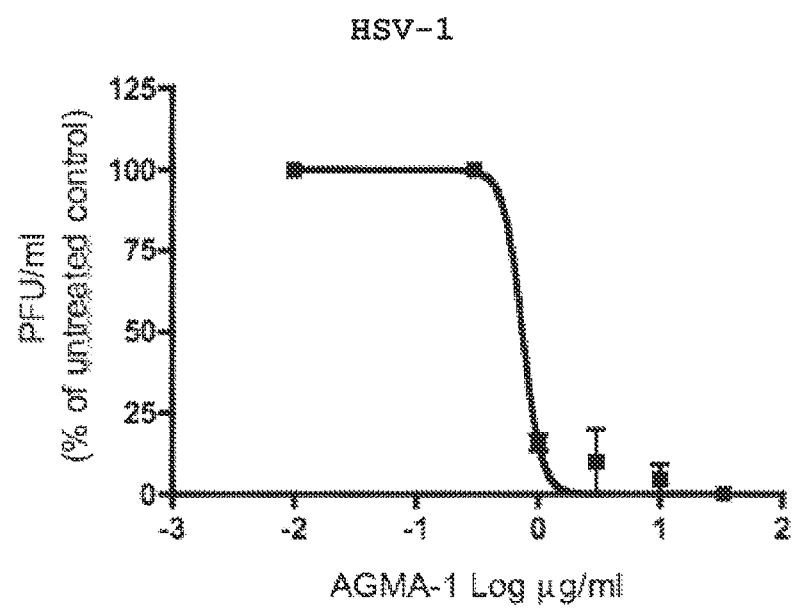
FIG. 4. Antiviral activity of AGMA-1 against HSV-1 (A) and HSV-2 (B).
Figure 4:
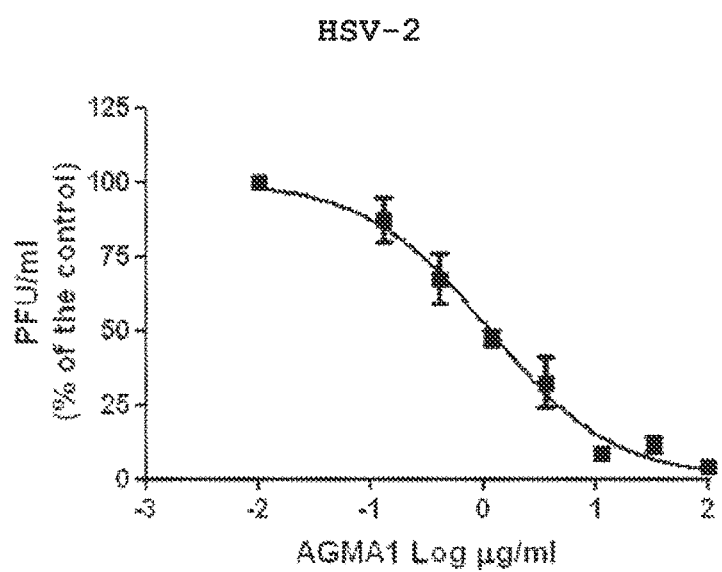

The dose-response curves shown in FIG. 4 and the corresponding IC50 values of 0.74 μg/ml and 1.14 μg/ml demonstrate the antiviral potency of the AGMA-1 compound against HSV-1 and HSV-2.

Example IV

Inhibition of HSV-2 Infection by AGMA1 in EpiVaginal Tissue

Tissues

The EpiVaginal Tissue Model (VEC-100/VEC-100-FT) were purchased from MatTek Corporation (Ashland, Ma., USA) and consist of Human 3-D Vaginal-Ectocervical Tissues that have been cultured to form a multilayered and highly differentiated tissues closely resembling that of epithelial tissue in vivo. According to the supplier's instructions, EpiVaginal cultures were transferred to 6-well plates (containing 0.9 ml of MatTek assay medium (VEC-100-ASY) per well)—with the apical surface remaining exposed to air—and incubated at 37° C. in 5% $CO_2$ overnight.

Antiviral Assay in EpiVaginal Tissue

EpiVaginal cultures were pre-incubated with AGMA1 by applying 100 μl medium containing 100 μg/ml of compound to the apical surface for two hours at 37° C. After pre-treatment, the medium was removed and cultures were infected with 1000 pfu of HSV-2 for two hours at 37° C. in presence of AGMA1. Cultures were washed apically with 100 μl of medium and placed at 37° C. and fed each day via the basolateral surface with 0.9 ml medium. Viruses were harvested by adding 100 μl medium per well to the Epivaginal Tissue's apical surface and allowed to equilibrate for 30 minutes at 37° C. The suspension was then collected and stored, at −80° C. until viral titers were determined by plaque assay in Vero cell monolayers. The viral collection was performed sequentially on the same wells of cells on each day post-infection.

Inhibitory Effect of AGMA-1 HSV-2 Infection in EpiVaginal Tissue

Figure 5:
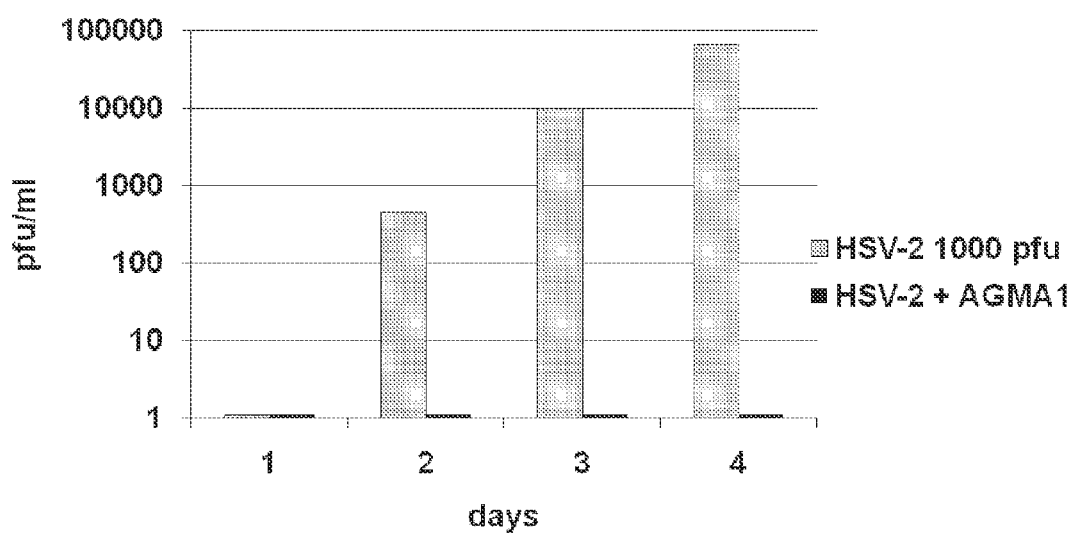
FIG. 5. Inhibition of HSV-2 infection by AGMA1 (100 μg/ml) in EpiVaginal Tissue.

The EpiVaginal Tissue Model closely resembles native human tissues, thus providing a useful in vitro means to assess sexually transmitted infections, like HSV-2 infection. We assessed the effect of 100 μg/ml of AGMA1 on HSV-2 infection in EpiVaginal cultures. The titer of virus emerging from the apical surface was measured at 24, 48, 72 and 96 hours post infection. FIG. 5 shows that at all days post, infection AGMA1 inhibited the viral titer by 100%. These result provided support for the efficacy of AGMA1 in the natural host.

Example V

Formulation of AGMA-1 Topical Gel

A solution of AGMA1 was prepared at a concentration of 150 mg/m in filtered water and the pH was adjusted at 5.5.

Gel formulations were obtained adding Pluronic F 127 in the concentration range from 2% to 12%.

AGMA1 may be present in the formulation in a concentration in the range of 50 mg/mL to 500 mg/mL.

Naturally, while the principle of the invention remains the same, the details of construction and the embodiments may widely vary with respect to what has been described and illustrated purely by way of example, without departing from the scope of the present invention.

REFERENCES

Buck, C. B., Pastrana, D. V., Lowy, D. R., & Schiller, J. T. (2004), "Efficient intracellular assembly of papillomaviral vectors" *J Virol* 78, 751-757.

Buck, C. B., Thompson, C. D., Pang, Y. Y., Lowy, D. R., & Schiller, J. T. (2005a). "Maturation of papillomavirus capsids" *J Virol* 79, 2839-2846.

Buck, C. B., Pastrana, D. V., Lowy, D. R., & Schiller, J. T. (2005b). "Generation of HPV pseudovirions using transfection and their use in neutralization assays" *Methods Mol Med* 119, 445-462.

Buck, C. B., et al., Carrageenan is a potent inhibitor of papillomavirus infection. PLoS Pathog, 2006. 2(7): p. e69.

Danusso, F., Ferruti, P. (1970). "Synthesis of tertiary amine polimers" *Polymer*, 11, 88-113.

Ferruti P., Marchisio M. A., Barbucci R. (1985). "Synthesis physico-chemical properties and biomedical applications of poly(amido-amine)s" *Polymer* 26, 1336-1348

Ferruti P. (1996). "Ion-Chelating Polymers (Medical Applications)", in: "*Polymeric Materials Encyclopedia*", vol. 5, J. C. Salamone, Ed. CRC Press INC, Boca Raton, Fla., 3334-3359

Ferruti P., Ranucci E., Trotta F., Gianasi E., Evagorou G. E., Wasil M., Wilson G., Duncan R. (1999). *Macromol. Chem. Phys.* 200, 1644.

Ferruti P., Marchisio M. A., Duncan R. (2002) "Poly(amido-amine)s: biomedical applications", *Macromol. Rapid. Common*, 23, 332-355.

Ferruti, P.; Franchini, J.; Bencini, M.; Ranucci, E.; Zara, G. P.; Serpe, L.; Primo, L.; Cavalli, R. (2007), "Prevailingly cationic agmatine-based amphoteric polyamidoamine as a nontoxic, nonhemolytic, and "stealthlike" DNA complexing agent and transfection promoter" *Biomacromolecules* 8, 1498-1504

Franchini, J.; Ranucci, E.; Ferruti, P.; Rossi, M.; Cavalli, R., (2006) "Synthesis, properties and preliminary biological characterizations of a novel amphoteric agmatine-based poly(amidoamine) with RGD-like repeating units" *Biomacromolecules*, 7, 1215-1222

Leder, C., et al., Enhancement of capsid gene expression: preparing the human papillomavirus type 16 major structural gene L1 for DNA vaccination purposes. J Virol, (2001) 75(19): p. 9201-9.

Pastrana, D. V., et al., Reactivity of human sera in a sensitive, high-throughput pseudovirus-based papillomavirus neutralization assay for HPV16 and HPV18. Virology, (2004). 321(2): p. 205-16.

Rusnati, M., Urbinati, C., Caputo, A., Possati, L., Lortat-Jacob, H., Giacca, M., Ribatti, D., & Presta, M. (2001). "Pentosan polysulfate as an inhibitor of extracellular HIV-1 Tat" *J. Biol. Chem.* 276, 22420-22425.

The invention claimed is:

1. A method of treating viral infections in a mammal in need thereof, said method comprising administering to said mammal an effective amount of antiviral agents comprising guanidine-based poly (amido-amine) polymer of formula (I):

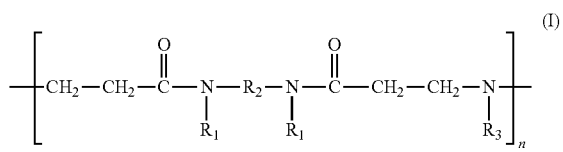

wherein n is an integer between 3 and 400;

R1 is H, C1-6 alkyl, or taken together with the N atoms to which is bound and R2 is a piperazinic ring;

R2 is C2-6 alkylen, C5-6 cycloalkylen, CH—COOH, CH—COOR, wherein R is C1-4 alkyl, phenyl or benzyl;

R3 is —(CH2)p-HN—C(NH2)=NH, wherein p is an integer 1 to 6;

or salt thereof.

2. The method according to claim 1, wherein R1 is H, R2 is CH—COOH and p equals to 4.

3. The method according to claim 1, wherein R1 is H, R2 is CH—COOH and p equals to 3.

4. The method according to claim 1, wherein R1 is H, R2 is H—COOH and p equals to 2.

5. The method according to claim 1, wherein R1 is H, R2 is CH—COOH and p equals to 5.

6. The method according to claim 1, wherein R1 is H, R2 is CH—COOH and p equals to 6.

7. The method according claim 1, wherein said guanidine-based poly (amido-amine) polymer is suitable for oral, parenteral, topical, nasal, rectal, ophthalmic and vaginal administration.

8. The method according to claim 7, wherein said effective amount is comprised between 50 and 500 mg when said guanidine-based poly (amido-amine) polymer is suitable for oral administration.

9. The method according to claim 7, wherein said effective amount is comprised between 2% and 50% w/w when said guanidine-based poly (amido-amine) polymer is suitable for parenteral administration.

10. The method according to claim 7, wherein said effective amount is comprised between 2% and 90% w/w when said guanidine-based poly (amido-amine) polymer is suitable for topical administration.

11. The method according to claim 1, wherein said viral infections are selected form the group consisting of HPV, HSV, HIV, human cytomegalovirus, Epstein-Barr virus, human herpesvirus 6, human herpesvirus 7, human herpesvirus 8 and adenovirus.

12. The method according to claim 1, wherein said mammal is a human being.

13. A method of treating viral infections in a mammal in need thereof, said method comprising administering to said mammal an effective amount of a pharmaceutical composition comprising at least one guanidine-based poly (amido-amine) polymer of formula (I):

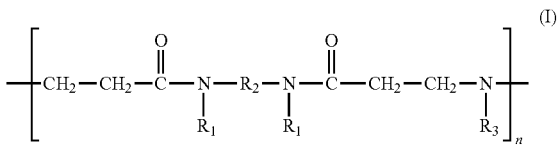

wherein n is an integer between 3 and 400;

R1 is H, C1-6 alkyl, or taken together with the N atoms to which is bound and R2 is a piperazinic ring;

R2 is C2-6 alkylen, C5-6 cycloalkylen, CH—COOH, CH—COOR, wherein R is C1-4 alkyl, phenyl or benzyl;

R3 is —(CH2)p-HN—C(NH2)=NH, wherein p is an integer 1 to 6, or salts thereof, and a pharmaceutically acceptable carrier and/or excipient.

14. The method according to claim 13, wherein said mammal, is a human being.

15. The method according to claim 13, wherein said pharmaceutical composition is suitable for oral, parenteral, topical, nasal, rectal, ophthalmic and vaginal administration.

16. The method according to claim 15, wherein said composition when suitable for oral administration contains said at least one guanidinebased poly (amido-amine) polymer in an amount comprised between 50 and 500 mg.

17. The method according to claim 15, wherein said composition when suitable for parenteral administration contains said at least one guanidine-based poly (amido-amine) polymer in an amount comprised between 2% and 50% w/w.

18. The method according to claim 15, wherein said composition when suitable for topical administration contains said at least one guanidinebased poly (amido-amine) polymer in an amount comprised between 2% and 90% w/w.

19. The method according to claim 13, wherein said viral infections are selected form the group consisting of HPV, HSV, HIV, human cytomegalovirus, Epstein-Ban virus, human herpesvirus 6, human herpesvirus 7, human herpesvirus 8 and adenovirus.

* * * * *